United States Patent [19]

Le Ribault et al.

[11] Patent Number: 4,994,445
[45] Date of Patent: Feb. 19, 1991

[54] SUBSTANCES WITH THERAPEUTIC APPLICATIONS COMPRISING ORGANO-SILICON COMPOUNDS

[75] Inventors: Loic Le Ribault, 23 chemin des Dames, 33260 La Teste Du Buch; René Nardou, 32 Allée Emile Péreire, 33120 Arcachon, both of France

[73] Assignees: Loic Le Ribault, La Teste de Buch; Rene Nardou, Arcachon; Michel Bonnaval-Lamothe, Cadillac-sur-Garonne, all of France

[21] Appl. No.: 498,444

[22] Filed: Mar. 22, 1990

Related U.S. Application Data

[63] Continuation of Ser. No. 212,094, Jun. 27, 1988, abandoned, which is a continuation of Ser. No. 699,257, Feb. 7, 1985, abandoned.

[30] Foreign Application Priority Data

Feb. 8, 1984 [FR] France .............................. 84 02120

[51] Int. Cl.$^5$ .................. A61K 33/00; A61K 31/695; C07F 7/18
[52] U.S. Cl. ...................................... 514/63; 424/617; 424/646; 424/649; 424/650; 424/655; 424/663; 424/718
[58] Field of Search .................. 514/63; 424/617, 646, 424/649, 650, 655, 663, 718

[56] References Cited

FOREIGN PATENT DOCUMENTS

| 828140 | 11/1969 | Canada | 514/63 |
| 56-22732 | 3/1981 | Japan | 514/63 |
| 56-26910 | 3/1981 | Japan | 514/63 |
| 1032175 | 6/1966 | United Kingdom | 514/63 |

Primary Examiner—Nathan M. Nutter
Attorney, Agent, or Firm—Fulbright & Jaworski

[57] ABSTRACT

A substance with therapeutic applications comprises, in aqueous solution:

(1) at least one organo-silicon compound having either of the following formulas:

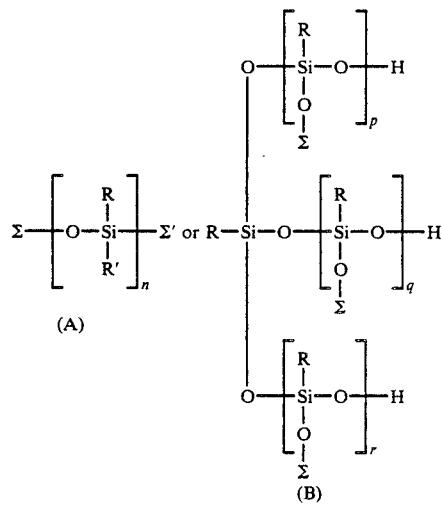

in which:
n is an integer between 1 and 1000, and preferably between 1 and 50;
p, q, r are integers between 0 and 1000, and preferably between 0 and 60;
R and R' represent, independently of one another, a linear aliphatic group, branched or cyclic, saturated or not, hetero-linear branched or not, cyclic saturated or not, aromatic, heteroaromatic, arylaliphatic, or heteroarylaliphatic, which may also be functional, whilst R may also be OH, OR or $OSiR_3$;
Σ is R, H or $SiR_3$, where R is as previously defined;
Σ' is R and more particularly $CH_3$, OR, OH or $OSiR_3$, where R is as defined above, and (2) at least one metal selected from the group comprising titanium, zirconium, hafnium, vanadium, germanium, chromium, rhodium, gold, iridium, platinum, osmium, the rare earths and uranyl derivatives, preferably in the form of a salt, an oxide or a hydroxide.

19 Claims, No Drawings

SUBSTANCES WITH THERAPEUTIC APPLICATIONS COMPRISING ORGANO-SILICON COMPOUNDS

This application is a continuation of application Ser. No. 07/212,094 filed June 27, 1988 and now abandoned which is a continuation of application Ser. No. 699,257 filed Feb. 7, 1985 and now abandoned.

BACKGROUND OF THE INVENTION

1. Field of the invention

The present invention concerns new substances with therapeutic applications, usable in particular to treat certain troubles of cellular mitosis and cardiovascular diseases.

2. Description of the prior art human beings for many years, due in particular to the discoveries of N. DUFFAUT.

These water-soluble and atoxic compounds pass easily through the epidermis and dermis on local application (GUEYNE, DUFFAUT and QUILICHINI, Thérapie 1962, 17, 417).

The numerous therapeutic properties of these organo-silicon compounds used on their own have been disclosed in several patents (in particular French Pat. Nos. 2.158.068, 2.160.293 and 2.230.376).

According to these documents, organo-silicon compounds are administered by intraveinous or intramuscular injection or by electrophoresis, the active ingredient being then in solution in water (isotonic solution), with the possible addition of an alcohol or polyalcohol, such as glycerol and/or a sodium salt of a pharmaceutically acceptable organic acid.

It has previously been shown, in particular in the above mentioned patents, that certain substances of various kinds are able to potentiate and widen the scope of the organo-silicon compounds.

It has now been unexpectedly found that it is possible to obtain a new substance with therapeutic applications by combining one or more organo-silicon compounds with one or more metals, preferably in the form of their salts (chloride, nitrate, sulfate or organic acid salt, for example) or in the form of oxides or hydroxides, all this by way of example with no limiting effect.

The metals concerned are titanium, zirconium, hafnium, vanadium, chromium, germanium, rhodium, gold, iridium, platinum and/or osmium, but use may also be made of uranyl derivatives and the rare earths.

It has also been found that substances of this type are especially useful for treating certain troubles of cellular mitosis and cardiovascular diseases against which they have a specific action, and that the substances thus obtained can be simply administered transcutaneously.

SUMMARY OF THE INVENTION

In one aspect, the invention consists in a substance with therapeutic applications, usable in particular for treating troubles of cellular mitosis and cardiovascular diseases, comprising, in aqueous solution:

(1) at least one organo-silicon compound having either of the following formulas:

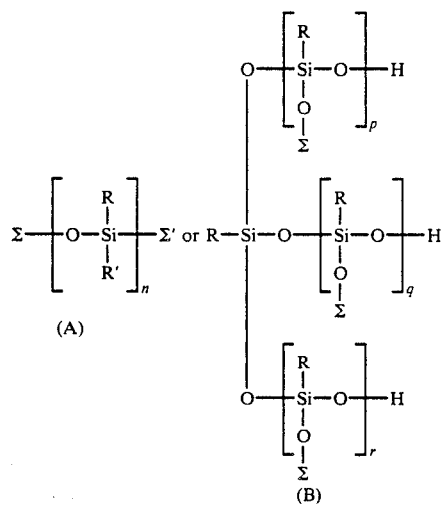

in which :

n is an integer between 1 and 1 000, and preferably between 1 and 50;

p,q,r are integers between 0 and 1 000, and preferably between 0 and 60

R and R' represent, independently of one another, a linear aliphatic group, branched or cyclic, saturated or not, hetero-linear branched or not, cyclic saturated or not, aromatic, heteroaromatic, arylaliphatic, or heteroarylaliphatic, which may also be functional, whilst R may also be OH, OR or $OSiR_3$;

$\Sigma$ is R, H or $SiR_3$, where R is as previously defined;

$\Sigma'$ is R and more particularly $CH_3$, OR, OH or $OSiR_3$, where R is as defined above, and (2) one or more metals preferably in the form of salts (chloride, nitrate, sulfate or organic acid salt, for example) or in the form of oxides or hydroxides without these forms having any limiting effect.

The organo-silicon(s) compound(s) is/are used in a concentration varying from $10^{-5}$ to $10^{-10}$ atom-gram of silicon per liter and more particularly $10^{-2}$ to $10^{-4}$ atom The metals usable are titanium, zirconium, hafnium, vanadium, germanium, chromium, rhodium, gold, iridium, platinum and/or osmium, but use may also be made of uranyl derivatives or the rare earths.

The proportions of the addition of (2):(1) are comprised between $10^{-10}$ and $10^{-5}$ atom-gram of metal per per liter of solution, but these proportions may be significantly reduced by using the metal elements in the form in which they are employed in homeopathy (preferably 5 to 20 granules at the dilution defined for homeopathy of 5 CH (CH=Hahnemann centesimal) in a liter of organo-silicon solution, nevertheless this dilution may vary very widely, from 20 CH to 1 D (D =Hahnemann decimal), and the concentration may be even higher as mentioned hereinabove).

The substance in accordance with the invention may also comprise, in a proportion appropriate to neutralizing and possibly stabilizing these substances, one or more organic acids (or their salts, in particular their alkaline salts), such as for example salicylic acid, citric acid, propionic acid, aspartic acid, glutaric acid, glutamic acid. It should however be noted that salicylic acid must be proscribed for the treatment of patients allergic to phenols and to salicylic acid in particular and that, to the extent that this situation may be encountered, it is then entirely possible to substitute for this acid citric acid or its salts, as is shown later in the examples.

The organic acid or its salt is in practice employed at concentrations varying from $10^{-5}$ to $10^{-1}$ molecule-gram per liter or more, and more particularly from $10^{-2}$ to $10^{-4}$ molecule-gram per liter.

In all cases, it would seem preferable that the solution have a pH between 3 and 7, or better still between 3 and 5.

The organo-silicon compounds corresponding to the above stated formula are products known per se.

There may be used for obtaining the substances in accordance with the invention either those available commercially or their known precursors from which they are obtained by hydrolysis, such as for example the corresponding silazanes or alcoxysilanes (in this context see in particular document FR-A-2.230.376 the text of which is herein incorporated by way of reference).

The metals may be combined with the organo-silicon compounds by addition to the solution of the latter either in the solid state or in the form of an appropriately titrated aqueous solution, either from the outset or at the time of application and in particular at the time of the use for therapeutic purposes of the substance in accordance with the invention.

The substance in accordance with the invention may thus consist either in a single product containing the organo-silicon compound and the metals or in a two-component product containing separately the organo-silicon compound and the metals, which may be mixed together extemporaneously.

The substance may be made available to users in bottles or in ampoules which constitute unit doses containing a measured quantity of product for each application.

The unit doses of the complete substance recommanded for each transcutaneous application are advantageously 200 cm$^3$ approximately.

The substances may further comprise neutralizing and/or preservative agents compatible with the active ingredients, such as those indicated hereinabove, as as other constituents such as coloring agents, scents and other excipients, such as the man skilled in the art is able to select and incorporate on the basis of his own knowledge and according to requirements.

From tests carried out on man, it has been possible to establish that applying organo-silicon compounds associated with metals, in the form of application of substances in accordance with the invention to the skin, as a compress, for example, has a transcutaneous action and exerts an action which is pharmacologically effective for the treatment of certain troubles of cellular mitosis and cardiovascular diseases.

The results of tests show that substances in accordance with the invention are particularly indicated and exceptionally effective, without having any significant toxicity, for the treatment or prevention of certain troubles of cellular mitosis and the treatment of cardiovascular diseases.

By way of indication, the following dosage may be recommanded:

Application of a cotton compress (approximately 5 cm by 7 cm) impregnated with the substance in accordance with the invention to the painful or deficient area or any other part of the body. The compress is covered with a film of plastics material or any other material able to retain moisture. The compress is applied for a period of between eight and twelve hours per day (overnight, for example).

Dabbing the skin with wadding impregnated with the substance in accordance with the invention. Dabbing is carried out two to four times per day, on the forearm, for example at the place where the blood vessels are most apparent. It has been possible to establish that the substance in accordance with the invention passes readily through the epidermis.

It has also been possible to apply simultaneously the constituents of the substance in accordance with the invention by ionokinesis practised locally at (or outside) the deficient or painful area. The ionokinesis equipement consists of a direct current generator (generating approximately 10-15 milliamperes) provided with a device for progressively establishing or interrupting the current and capable of maintaining a constant current throughout the duration of the treatment. The current is progressively increased to 10 mA and maintained for twenty minutes before it is progressively reduced and then interrupted. In certain cases, the current may be increased to 25 mA, the duration of the treatment possibly being as much as 30 minutes. The generator is connected to two electrodes of carbon or other materials as routinely used for ionokinesis treatment. The surface area of the electrode, although varying widely, is routinely on the order of 200 cm$^2$. Each of the two electrodes is surrounded with hydrophilic cotton impregnated with the substance in accordance with the invention.

The electrode connected to the negative terminal of the generator is applied to any part of the body, preferably the deficient or painful area; it is held in contact with the skin by means of a bandage. The other electrode, connected to the positive terminal of the generator, may be applied to any location on the skin or merely held in the hand, the area of contact being as large as possible. In certain special cases the polarity of the electrodes is reversed during the treatment.

It should be indicated that a course requires ten to thirty treatments at intervals of twenty-four through seventy-two hours, the rate most routinely adopted being two to three treatments per week. The course is totally without pain. However, certain sensitive subjects experience a pricking sensation at the location of the electrodes during the treatments. No local or general reaction of the organism has been noted, except slight erythema in the area to which the electrodes are applied.

However, when the subject is allergic to phenol derivatives, a solution not containing this type of derivative must be selected.

Intramuscular injections may also be used.

EXAMPLES

The invention will now be described in more detail with reference to the following non-limiting examples.

EXAMPLE 1

Into a 1 liter beaker was placed 1 g of salicylic acid to which 700 ml of distilled water was added.

Whilst stirring vigorously, 1.2 ml of potassium extract) was slowly added. Then 1 mg of uranyl nitrate was added. The pH of the solution was adjusted to 4.7 by adding an aqueous solution of potassium and the volume made up to 1 liter with distilled water.

EXAMPLE 2

Into a 1 liter beaker was placed 1 g of citric acid to which 70 ml of distilled water was added.

Whilst stirring vigorously, 1.2 ml of potassium methylsiliconate solution (concentration 45% of dry extract) was slowly added. Added in succession were 3 mg of zirconium nitrate, 1 mg of uranyl nitrate, 1 mg of hafnium nitrate and 3 mg of titanium chloride.

The pH of the solution was then adjusted to 4.7 by adding an aqueous solution of potassium the volume was made up to 1 liter with distilled water and the solution filtered.

EXAMPLE 3

Into a beaker containing 500 ml of distilled water previously cooled by addition of crushed ice there was slowly added whilst stirring vigorously 0.65 g of dimethyldichlorosilane and 0.85 g of sodium bicarbonate.

It was verified that the pH was approximately 7.

The solution thus obtained being homogeneous, there was added slowly whilst stirring vigorously 1.1 g of sodium salicylate.

2 mg of zirconium nitrate was added.

The pH of the solution was adjusted to 4.7 by addition of an aqueous solution of soda.

The volume was then made up to 1 liter with distilled water.

EXAMPLE 4

Into a beaker was placed 1 g of citric acid to which 700 ml of distilled water was added.

Whilst stirring vigorously, 1.7 ml of a solution of potassium methylsiliconate (concentration 45% of dry extract) was slowly added to this solution.

1 mg of uranyl nitrate was added.

The pH of the solution was adjusted to 4.7 by addition of an aqueous solution of potassium. The volume was then made up to 1 000 ml with distilled water.

EXAMPLE 5

Into a 1 liter beaker was placed I g of salicylic acid to which 700 ml of distilled water was added.

Whilst stirring vigorously, 1.2 ml of a solution of potassium methylsiliconate (concentration 45% of dry extract) was slowly added. There was then added 3 mg of zirconium nitrate. The pH of the solution was adjusted to 4.7 by addition of an aqueous solution of potassium and the volume was made up to 1 liter with distilled water.

To illustrate the pharmacological properties of the substances comprising in combination an organo-silicon compound as stated hereinabove and metals in accordance with the invention, there are described hereinafter examples of pharmacological tests relating to the treatment of cardiovascular diseases and certain troubles of cellular mitosis (particularly cancer) in man.

TEST 1

Beatrice ART . . . has a very extensive epitheliomatous invasion of the left lung detected by radiological and tomographic examination. The course is carried out in the following manner for two months using the substance as in example 1 hereinabove:

daily compress for eight hours.,
dabbing of the forearms four times per day.

Further radiological examination carried out two and a half months afterwards indicates significant regression of the lesions and a clear clinical improvement.

The course is continued for a further month.

A further radiographic examination indicates disappearance of pathological signs.

Three years later the patient is still in good health.

TEST 2

Henri AUG . . . has continuous pain in the lower left thorax, accompanied by respiratory difficulty and a dry cough. Clinical examination shows shrinkage of the left hemithorax; radiography shows a large and irregular mass in the left lung and numerous localized sites of decalcification of the ribs. A costal biopsy shows invasion by neoplasmic epithelial formations.

The course is carried out in the following manner for three months using the substance as in example 2 hereinabove:

daily compress for eight hours;
dabbing of the forearm four times per day;
twenty-five ionokinesis treatments.

After three months radiographs show total melting away of the pulmonary mass and recalcification of the ribs.

The course is continued for three months.

After three years the condition of the patient is satisfactory.

TEST 3

Lucien DAV . . . has for a few years suffered from precordial pain on walking and exertion, for which he is obliged to take trinitrine in amounts of three to six tablets per day.

The course is carried out in the following manner for two weeks using the substance as in example 3 hereinabove:

daily compress for eight hours;
dabbing of forearms three times per day.

After fifteen applications, the painful attacks are seen to disappear and the patient stops taking trinitrine.

The patient continues with local maintaining applications twice per week.

After three months the condition of the patient is satisfactory. The electrocardiogram is normal

TEST 4

Raoul TRA . . . suffers diffuse epigastric pains interspersed with paroxysmal episodes.

Clinical examination shows a subicterus. Surgical investigation shows neoplasmic invasion of the pancreas.

By virtue of the extent of the lesions, the surgeon decides not to take further action and closes the incision.

The course is carried out in the following manner for one month using the substance as in example 4 hereinabove:

daily compress for eight hours;
dabbing of forearms four times per day. At the end of a month the treatment leads to disappearance of the subicterus and pain.

The course is continued for several weeks.

After one year the patient is in good health.

TEST 5

Marcel DUR . . . has suffered a myocardial infarction. The electrocardiogram shows signs of posterior infarction and he suffers residual angina pectoris characterized by precordial pain on walking and exertion.

The course is carried out in the following manner for three months using the substance as in example 5 hereinabove:

a daily compress for eight hours;
dabbing of the forearms three times per day;
twenty ionokinesis treatments.

After this course, signs of ischemia disappear; there remain on the electrocardiogram only discrete signs of posterior necrosis.

Maintaining applications are continued at the rate of three per week.

After six months the electrocardiogram is again normal and the state of health of the patient is satisfactory.

We claim:

1. A composition for the treatment of cardiovascular diseases and having therapeutic value, comprising in aqueous solution:

(1) at least one organo-silicon compound having either of the following formulae:

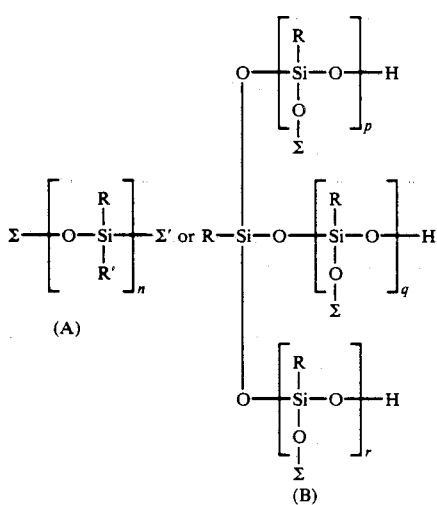

in which:
    n is an integer between 1 and 1000;
    p, q, and r are integers between 0 and 1000;
    R and R', independently of one another, represent saturated or unsaturated linear, branched or cyclic groups which may include hetero-linear, aromatic, heteroaromatic, arylaliphatic or heteroarylaliphatic groups, with R further representing OH, OR, or $OSiR_3$, where R is as described above;
    being R, H, or $SiR_3$ where R is as defined above;
    being R where R is as defined above; and (2) at least one metal selected from the group consisting of titanium, zirconium, hafnium, vanadium, germanium, chromium, rhodium, gold, iridium, platinum, osmium, rare earths, and uranyl derivatives;
    said organo-silicon compound being present in said composition in an amount between about $10^{-5}$ to $10^{-1}$ gram-atom of silicon per liter and the weight/volume ratio of (2):(1) is between about $10^{-10}$ to $10^{-5}$ gram-atom of metal per liter of solution.

2. A composition according to claim 1, wherein said organo-silicon compound comprises an alkaline methylsiliconate.

3. A composition according to claim 1, wherein the weight/volume ratio (2):(1) is between the values of 200 CH and 1 D (homeopathic units).

4. A composition according to claim 1, further comprising an effective amount for said treatment of an organic acid selected from the group consisting of salicylic acid, citric acid, propionic acid, aspartic acid, glutaric acid, glutamic acid and salts thereof.

5. The composition according to claim 1 wherein n ranges from between 1 and 50.

6. The composition according to claim 1 wherein p, q and r range from between 0 and 60.

7. The composition according to claim 1 wherein $\Sigma'$ is selected from the group consisting of $CH_3$, OR, OH and $OSiR_3$.

8. The composition according to claim 1 wherein said organo-silicon compound is present in a concentration in the range of from $10^{-4}$ to $10^{-2}$ gram-atom per liter.

9. The composition according to claim 1 wherein said metal is present in the form of a salt, oxide, or hydroxide.

10. A method for the treatment of cardiovascular diseases, comprising transcutaneously administering to a human a therapeutically effective amount for said treatment of an aqueous composition comprised of:

(1) at least one organo-silicon compound having either of the following formulae:

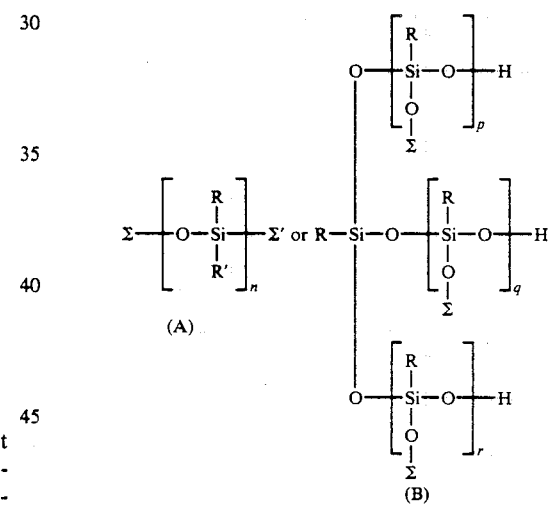

in which:
    n is an integer between 1 and 1000;
    p, q, and r are integers between 0 and 1000;
    R and R', independently of one another, represent saturated or unsaturated linear, branched or cyclic groups which may include hetero-linear, aromatic, heteroaromatic, arylaliphatic or heteroarylaliphatic groups, with R further representing OH, OR, or $OSiR_3$, where R is as described above;
    being R, H, or $SIR_3$ where R is as defined above;
    being R where R is as defined above; and (2) at least one metal selected from the group consisting of titanium, zirconium, hafnium, vanadium, germanium, chromium, rhodium, gold, iridium, platinum, osmium, rare earths, and uranyl derivatives;
    said organo-silicon compounds being present in said composition in an amount between about $10^{-5}$ to $10^{-1}$ gram-atom of silicon per liter and the weight/volume ratio of (2):(1) is between about $10^{-10}$ to $10^{-5}$ gram-atom of metal per liter of solution.

11. The method according to claim 10 wherein n ranges from between 1 and 50.

12. The method according to claim 10 wherein p, q and r range from between 0 and 60.

13. The method according to claim 10 wherein $\Sigma'$ is selected from the group consisting of $CH_3$, OR, OH and $OSiR_3$.

14. The method according to claim 10 wherein said organo-silicon compound is present in a concentration in the range of from $10^{-4}$ to $10^{-2}$ gram-atom per liter.

15. The method according to claim 10 wherein said metal is present in the form of a salt, oxide, or hydroxide.

16. The method according to claim 10 wherein said composition is administered in the form of unit doses of about 200 $cm^3$.

17. The method according to claim 10, wherein the weight/volume ratio (2):(1) is between the values of 20 CH and 1D (homeopathic units).

18. The method according to claim 10, wherein said organo-silicon compound comprises an alkaline methylsiliconate.

19. The method according to claim 10, further comprising an organic acid selected from the group consisting of salicylic acid, citric acid, propionic acid, aspartic acid, glutaric acid, glutamic acid and salts thereof.

* * * * *